United States Patent [19]
Eigenbrodt et al.

[11] Patent Number: 5,972,628
[45] Date of Patent: Oct. 26, 1999

[54] PYRUVATEKINASE-IOSENZYME TYP-M2 (TUMOR-M2-PK)-SPECIFIC ANTIBODY/ PROCESS FOR THE PREPARATION AND USE THEREOF

[75] Inventors: Erich Eigenbrodt, Linden; Manfred Reinacher, Giessen; Ursula Scheefers-Borchel; Hans Scheefers, both of Wettenberg, all of Germany

[73] Assignee: ScheBo Tech Medizinisch-Biologische Forschungsgesellschaft m.b.H., Wettenberg, Germany

[21] Appl. No.: 08/303,892

[22] Filed: Sep. 9, 1994

Related U.S. Application Data

[63] Continuation of application No. 07/688,952, May 8, 1992, abandoned.

[30] Foreign Application Priority Data

May 8, 1992 [WO] WIPO ...................... PCT/EP89/01384

[51] Int. Cl.⁶ ........................ G01N 33/53; G01N 33/574; C07K 16/40; C12N 5/20
[52] U.S. Cl. ........................ 435/7.23; 435/7.1; 435/7.2; 435/7.4; 435/7.92; 435/7.93; 435/7.94; 435/7.95; 435/975; 435/330; 435/337; 435/338; 435/344; 435/344.1; 530/388.26; 530/388.25; 530/391.3; 530/808; 530/809; 530/388.8; 530/388.85; 530/389.7; 436/518; 436/536; 436/811
[58] Field of Search ........................ 424/174.1; 435/7.1, 435/70.21, 172.2, 240.27, 7.23, 7.2, 7.4, 7.92, 7.93, 7.94, 7.95, 975, 330, 337, 338, 344, 344.1; 530/388.8, 388.85, 389.7, 388.26, 388.25, 391.3, 808, 809; 436/518, 536, 811

[56] References Cited

U.S. PATENT DOCUMENTS

| | | | |
|---|---|---|---|
| 4,396,520 | 8/1983 | Payne et al. | 252/89.1 |
| 4,536,319 | 8/1985 | Payne et al. | 252/174.17 |

FOREIGN PATENT DOCUMENTS

| | | |
|---|---|---|
| 0070074 | 1/1983 | European Pat. Off. . |
| 0280143 | 8/1988 | European Pat. Off. . |
| 8600992 | 2/1986 | WIPO . |
| 8602943 | 4/1986 | WIPO . |
| 8703094 | 5/1987 | WIPO . |

OTHER PUBLICATIONS

Eigenbrodt et al., Crit. Rev. Oncogenesis, 3: 91–115, 1992.
Scheefers–Borchel et al., "Quantitative determination (ELISA) of pyruvak tumor M2–A new tumor marlaer", from: Current Tumor Diagnosis: Applications Clinical Relevant Research –Trends Ed. R. Klipdoor, Zuckschwerdt Verb., GmbH, 1994, pp. 365–368.
Seaver, Gen. Eng. News, 14: 10 and 21, 1994.
Harris, TIBTECH, vol. 11, pp. 42–44, 1993.
Weernink et al., Chem Ab, vol. 109, p. 619, No. 228157.
Reinacher et al., Virchows Arch, vol. 37, 79–88, 1981.
Erp et al., Eur. J. Cell Biology, 47, 388–394, 1988.
Heinrichs et al., Biomed. Biochim. Acta 46, 213, S 223–228, 1987.
Weernink et al., Febs Letters, vol. 236, #2 391–395, 1988.
Eigenbrodt et al., Biomed. Biochim. Acta, 42 (1983) 11/12, S 278–282, 1983.
Goldenberg, Arch Pathol. Lab. Med., vol. 112, 580–587, 1988.
Nakamura et al., Enzyme immunoassays, Chapter 27 from Handbook of Exp Immunol., vol. 1, DW Weir ed, Blackwell Sci, 1986.
Goding, Monoclonal Antibodies: Principles and Practice; Section 2.6.2, Chapter 3, Section 8.1.2, Academic Press, 1986.
Waldman, Science, vol. 262, p. 1657–1662, 1991.

*Primary Examiner*—Ronald B. Schwadron
*Attorney, Agent, or Firm*—Nikaido, Marmelstein, Murray & Oram LLP

[57] ABSTRACT

A qualitative, quantitative, as well as local determination of pyruvatkinase (ATP:pyruvate-2-O-phosphotransferase, EC 2.7.1.40)-isoenzyme typ M2 (Tumor-M2-PK) is possible in blood, plasma, tissue culture, tissue sections as well as in the animal and human organism with the help of antibodies.

Corresponding antisera are obtained if highly purified pyruvatekinase-isoenzymes type M2 (Tumor-M2-PK) or fragments of these, are used as immunogen. Preferable are antisera with monoclonal antibodies.

These antibodies can be used in ELISA-Test systems for the diagnosis of cancer, to determine the malignancy of cells, to localize a tumor in an organism as well as for the therapy of cancer.

9 Claims, No Drawings

PYRUVATEKINASE-IOSENZYME TYP-M2 (TUMOR-M2-PK)-SPECIFIC ANTIBODY/ PROCESS FOR THE PREPARATION AND USE THEREOF

This application is a continuation of application Ser. No. 07/688,952, filed May 8, 1992, now abandoned.

DESCRIPTION

The invention is concerned with a process to determine selectively the human pyruvatekinase (ATP: pyruvate-2-0-phosphotransferase, EC 2.7.1.40)-isoenzyme type M2 (Tumor-M2-PK) in plasma, blood or tissue using highly specific antibodies, with the antibodies required therefor, which bind specifically to Tumor-M2-PK and discriminate between other pyruvatekinase-isoenzymes (M1, L and R-type), with a use thereof and with a reagent containing them.

Introduction

Today, cancer diseases belong beside cardiovascular diseases to the most predominant cause of mortality in countries with a good medical supply. In these countries about one quarte of mortalities are due to the appearence of malignant tumors. F. W. MacKay Cancer Mortality in the United States 1950–1977. National Cancer Department Monograph Vol. 59 U.S. Government Printing Office 1982; R. W. Miller and F. W. McKay, J. Am. Med. Ass. 251, 1567 (1984).

It is expected that this percentage will increase parallel to increasing life expectancy.

The medical treatment of cancer diseases is multiple, because not "the cancer" is existent but more than hundred different types are known. Although during the past years remarkable knowledge about cancer development could be obtained, the pathogenesis of malignant tumors is in many respects completely unsolved. It can be said, however, that for one reason cancer is evoked by mutations of genes which trigger the growth and differentiation of cells (somatic mutation theory) D. Harden: Progress in Cancer Research and Therapy Bd. III p. 87 Raven Press, New York 1977 or by the other reason is based upon a disregulation of gene expression (theory of abnormal differentiation) A. Upton: Cancer, Principles and Practice of Oncology p. 33. J. B. Lippincott Company, Philadelphia Toronto 1982.

Considerably reliable is the assumption that in some cases cancer is induced by the activation of viral DNA or RNA which has been inserted as an oncogene into the genome of the host cell. J. M. Bishop, Anual. Rev. Biochem. 52, 301 (1983); R. A. Weinberg Science 230, 770 (1985).

A direct correlation between the influence of naturally and artificially, chemically and physically occuring noxes and the development of cancer could be demonstrated without doubt in some cases. (J. C. Acros, M. F. Argus and G. Wolf (Eds.): Chemical Induction of Cancer, Vol. 1, Academic Press, New York 1968).

For the detection of malignant occurence in an organism or for the discrimination between "normal" and "transformed" cells it is necessary to find out biochemical differences between abnormal and normal cells on a molecular basis, thereby the differentiation may be caused by the surface structure (Unger H. Eibl and G. A. Nagel (Eds.): Die Zellmembran als Angriffspunkt der Tumortherapie, Zuckschwerdt Verlag (1987)) or by the metabolism of cells (O. Bodansky, Biochemistry of Human Cancer, Academic Press, New York (1975)). Some biochemical differences between "normal" and malignant cells have been found. The use of these differences for a general and selective tumor therapy was not possible until now, because the differences have been found only in some forms of tumors and their quantity was not sufficient.

It is however remarkable that the mostly pronounced difference in the metabolism between normal and malignant cells is an increase in the rate of aerobic glycolysis in malignant cells. In 1930 already Warburg (O. Warburg: The Metabolism of Tumours Constable, London 1930) could demonstrate in in vitro experiments that the incubation of normal tissue in a buffered solution containing glucose no or almost no lactate was formed when oxygen was present, whereas under the same conditions in tumor tissue considerable amount of lactate was formed.

Before this Cori and Cori described that the application of glucose to mice bearing a mamma carcinoma resulted in an increased lactate formation (C. F. Cori and G. T. Cori, J. Biol. Chem. 64, 11 (1925); 65,397 (1925).

The increase in aerobic glycolysis could be demonstrated in almost all malignant cells of animal and human source.

State of Science and Techniques

In clinical chemistry tumors can be demonstrated by the detection of enzymes (acid phosphatase, gamma-GT or by substances like alpha fetoprotein, tissue polypeptid antigen, sialic acid and carcinoembryonic antigen. Herschmann, H. R. Trends Biochem. Sci. 5, 82–84 (1980); Stugeon, C. M. Trends Biochem. Sci. 4, 121–123.(1979); Schuster, J., Livingston, A., Banjo, C., Silver, H. K. B., Freedman, S. O. and Gold, P. (1975); Silver, H. K. B., Gold, P., Feder, S. and Schuster, J. (1973); Björklund, B. Tumor Diagnostik 1, 9–20 (1979); Björklund B., Wiklund, B., Lüning B., Anderson, K., Kallin, E. and Björklund V. Tumor Diagnostik 2, 78–84 (1980); Lüthgens, M. and Schlegel, G. Tumor Diagnostik 2, 63–77 (1980); Silver, K. B. H., Karim, K. A., Archibald, E. L. and Salinas, F. S. Cancer Res. 39, 5036–5042 (1979). The detection of an isoenzyme of the acid phosphatase in blood indicates with great certainty the presence of tumors of the prostata and its bone metastases. The specificity of this evidence could be enhanced by the introduction of an ELISA-Assay. Herschmann, H. R. Trends Biochem. Sci. 5, 82–84 (1980). The activity of gamma glutamyltransferase (gamma GT), which is enhanced in preneoplastic foci of liver in rat and mouse does not show a correlation between the grade of malignancy of tumors. Boelsterli, U. Trends Pharmacol. Sci. 1, 47–49 (1979). The carcinoembryonic antigen (CEA) is found to be enhanced in a variety of tumor diseases but also in non-carcinomatous diseases. The tissue polypeptide antigen (TPA) serves mainly as an indicator of mamma-tumors. Björklund, B., Tumor Diagnostik 1, 9–20 (1979). Also the alpha-fetoprotein has been essentially applied in the diagnosis and the control of liver-and germ cell tumor development. Abelev, G. K., Cancer Res;. 28, 1344–1350 (1968); Abelev, G. K., Adv. Cancer Res. 14, 295–358; Sell, S., Becker, F. F., Leffert, H. L. and Watabe Cancer Res. 36, 4239–4249 (1976).

Therefore all these tests are relatively high specific for certain tissues and can not be applied generally for the diagnosis of tumors. According to that, these tests are mostly applied to control therapy of known tumors than for tumor-screening and tumor-diagnosis. Koch, O. M. and Uhlenbruck, G. Med. Diagnostik 33, 29–38 (1983).

In contrast to this, investigations show, that tumor-M2-PK is present in all tumors, except those tumors, which originate from cells containing pyruvate kinase type L (hepatocytes).

The detection of pyruvate kinase isoenzyme tumor type M2 therefore provides a test for a tumor marker, which includes a broad spectrum of tumors Cooper, J. A., Reiss, N. A., Schwarz, R. J. and Hunter, T. Nature 302, 218–223 (1983); Reinacher, M. and Eigenbrodt, E. Virchows Archiv, 37, 79–88 (1981).

It would be desirable to be able to specifically detect pyruvatekinase Tumor-M2-PK as a tumor marker in blood, plasma, body fluids, swabs, tissues and/or tissue culture (biopsymaterial).

The determination of this tumormarker can be applied immunohistologically for the detection of micrometastases or even single tumor cells and can be used in sandwich-ELISA for testing blood, plasma, body fluids, swabs, tissues and tissue cultures. Furthermore, the determination of Tumor-M2-PK allows an insight into the actual metabolic status of tumor cells under oxygen defficiencies (hypoxic tumor cells). Furthermore rules can be drawn, on the ability to synthesize purines and to regenerate NADPH- and GSA, which are all targets for chemotherapy or which may have an influence on the metabolism of these substances.

It is an object of the present invention to provide a process for the quantitative, specific determination of Tumor-M2-PK which, in particular, allows the detection of very small amounts of Tumor-M2-PK, which process can be carried out very precisely and, in particular, makes possible the specific detection of Tumor-M2-PK without being disturbed by other pyruvate kinase isoenzymes or other proteins present in blood, plasma, body fluids or tissues of the human organism.

This object is achieved by a Tumor-M2-PK-specific antibody which is specifically bindable with Tumor-M2-PK and which discriminates between other substances.

Antisera which contain the antibodies used according to the present invention are obtained in that, into the organism of experimental animals, there are introduced as immunogen highly purified Tumor-M2-PK or fragments thereof.

Experimental animals, such as mice, rats, rabbits, goats or horses, are immunised in known matter and antisera are thus obtained with polyclonal antibodies. In a preferred embodiment, monoclonal antibodies are produced in appropriate manner according to the method of G. Köhler and C. Milstein, Nature, 256, 495–497/1975.

Therefore, a further subject of the present invention is a process for obtaining a monoclonal antibody which is specifically bindable with Tumor-M2-PK. In this process mice or rats are immunised with highly purified Tumor-M2-PK, B-lymphocytes from the spleen of the immunised animals are fusioned with myeloma cells, the hybridoma cells formed are cloned, the hybridoma cells secreting antibodies bindable with Tumor-M2-PK, are isolated, cloned and cultured and the monoclonal antibodies formed by them are recovered.

A cell line is preferably used which itself does not produce any immune globulin.

The monoclonal antibodies obtainable according to the present invention do not react with other pyruvate-kinase-isoenzymes or with other substances, but are specific for Tumor-M2-PK.

A further subject of the present invention is the use of the Tumor-M2-PK-specific antibody according to the present invention for the qualitative and/or quantitative determination of Tumor-M2-PK. Therefore it is possible, using this antibody to specifically determine Tumor-M2-PK in body fluids, tissues or swabs.

In experiments for the detection of pyruvatekinase isoenzymes in blood, plasma or serum, indirect, competitive and sandwich-ELISA have been applied. To be independent from factors which could not be calculated, a sandwich ELISA proved to be most suitable for the diagnosis especially when many samples had to be hand led.

For this assay at least two different monoclonal antibodies directed against different epitopes of the isoenzyme are necessary.

With these tests shifts of the isoenzyme pyruvatekinase M2 for example in serum can be demonstrated, especially the occurence of these shifts which accompany malignant diseases.

Determination processes according to the immunoassay principle are widely used. The advantage of these methods of determination is their exactitude and the possibility of being able to detect very small amounts of substances. Different process variants are possible for carrying out the determination, not only with homogeneous but also with heterogeneous phases. In the case of the embodiment with heterogeneous phases, one of the receptors is bound to a carrier. In the case of the sandwich process, for example, a receptor is bound to a carrier and the test solution is added thereto, the antigen to be determined and present in the test solution thereby being bound to the receptor. A labelled receptor is then added thereto which reacts specifically with the antigen or the antigen-antibody complex. The amount of antigen can then be calculated via the labelled antibody.

There are many possibilities of varying this general principle. Thus, for example, a determination can take place with three receptors, one of the three receptors being present in heterogeneous phase and the other two receptors being soluble, one of the two soluble receptors being labelled, whereas the other one is unlabelled. The soluble receptor is then directed against the unlabelled, soluble receptor.

The use of the Tumor-M2-PK-specific antibody according to the present invention for the selective, quantitative determination of Tumor-M2-PK according to the principle of immunoassay by incubation with at least two different receptors, of which the first receptor R1 is present in solid phase and is bindable with Tumor-M2-PK and a receptor, and at least one further receptor R2 is present in soluble phase which is bindable with Tumor-M2-PK and a receptor, one receptor R2 carrying a labelling, separation of the solid phase from the liquid phase and measurement of the labelling in one of the phases, wherein, as one of the receptors, there is used a Tumor-M2-PK-specific antibody which is specifically bindable with Tumor-M2-PK and discriminates between Tumor-M2-PK and between other pyruvatekinase isoenzymes.

At least two different receptors are used for carrying out this process, one of these receptors being specifically bindable with Tumor-M2-PK. At least one further antibody must also be bindable with Tumor-M2-PK. An antibody can hereby be used which binds Tumor-M2-PK nonspecifically and also binds with other pyruvatekinase isoenzymes. However, here too, a receptor is also used which is specifically bindable with Tumor-M2-PK.

One of the two receptors is bound to a solid phase, binding to the solid phase taking place in a manner known to the expert. Furthermore, at least one further receptor is used which is present in soluble form. This further receptor is labelled. If further receptors (R2) are used, then only one of them carries a labelling. The labelling of the receptor takes place in the usual manner known to the expert.

The labelling in a known manner preferably takes place by means of a radioactive compound, an enzyme or a chemiluminescent or fluorescing compound. The labelling is especially preferably carried out with an enzyme and particularly with peroxidase or phosphatase. The labelling by means of an enzyme allows in an especially preferred embodiment of the test and due to the state of the art, to use this antibody in a second enzyme-amplification-system. Stanley, C. J., Paris, F., Plumb, A., Webb, A. Johannsson, A. American Biotechnology Laboratory: May/June 1985; Self, C. H. J. Immunol. Meth. (1985), in press; Johannsson, A., Stanley, C. J., Self, C. H. Clin. Chem.Acta (1985) ; in press.

In an especially preferred embodiment of the process, to a solid phase there is bound either a receptor nonspecifically bindable with Tumor-M2-PK or preferably a receptor specifically bindable with Tumor-M2-PK. This receptor bound to the solid phase is subsequently incubated with the solution containing the Tumor-M2-PK to be determined and an antibody which is specifically bindable with the Tumor-M2-PK and is present in soluble form and carries a labelling. If the receptor bound to the solid phase is capable of nonspecific binding with Tumor-M2-PK, then there is attached to the solid phase not only Tumor-M2-PK but also other pyruvatekinase isoenzymes. The second antibody, which is specifically bindable with the Tumor-M2-PK, is then only attached to Tumor-M2-PK so that only the Tumor-M2-PK specifically carries a labelled antibody, whereas the other pyruvatekinase isoenzymes are not labelled. In this way, after separation of the solid phase from the liquid phase, it is possible to determine the content of Tumor-M2-PK via measurement of the labelling.

If, as solid phase-bound receptor, there is used a receptor which is specifically bindable with Tumor-M2-PK, then only Tumor-M2-PK is specifically bound to the solid phase and, in the case of incubation with the soluble antibody, this also again reacts specifically with the Tumor-M2-PK. Since practically no binding with other pyruvatekinase isoenzymes to the solid phase takes place, this process is even more specific and therefore permits very precise determinations.

In a further especially preferred embodiment of the process according to the present invention, an antibody specifically bindable against Tumor-M2-PK is immobilized on a carrier. With this immobilized antibody the solution is incubated containing the Tumor-M2-PK to be determined and a receptor which is bindable with Tumor-M2-PK, preferably a receptor which is specifically bindable with Tumor-M2-PK.

Thereby Tumor-M2-PK is being bound practically exclusively to the solid phase and other pyruvatekinase isoenzymes remaining in solution. Furthermore, the soluble, labelled antibody bindable with Tumor-M2-PK attaches to the Tumor-M2-PK. After separation of the solid phase from the liquid phase, the Tumor-M2-PK content can be determined very exactly via the labelling.

Further process variants known to the expert with three receptors are also possible with the use of the antibody specifically bindable with Tumor-M2-PK and do not here require further explanation.

Of the antibodies used for carrying out the process according to the present invention, preferably at least one is a monoclonal antibody. Especially preferably, as receptors are only used monoclonal antibodies.

A further subject of the present invention is a reagent for the selective determination of Tumor-M2-PK containing a receptor R1 bound to a solid phase which is bindable with Tumor-M2-PK and a receptor and at least one receptor R2 present in soluble phase which is bindable with Tumor-M2-PK and a receptor, a soluble receptor R2 thereby carrying a labelling, wherein one of the receptors is an antibody which is specifically bindable with the Tumor-M2-PK.

The antibody specifically bindable with the Tumor-M2-PK can be present either bound to the solid phase or can be used as soluble labelled or unlabelled receptor, this antibody preferably being a monoclonal antibody. Especially preferably, all the receptors used are monoclonal antibodies.

Furthermore, the Tumor-M2-specific antibody according to the present invention can advantageously be used for the qualitative determination of Tumor-M2-PK and Tumor-M2-PK coagula in the human blood circulation.

For this purpose, the Tumor-M2-PK specific antibody according to the present invention, especially preferably the monoclonal, Tumor-M2-PK- specific antibody prepared according to the present invention, is labelled, injected into the blood circulation and made visible by suitable means.

Especially preferably, patients are injected with the Tumor-M2-PK-specific antibody according to the present invention which has been radioactively labelled. The antibody then becomes enriched at coagula etc. metastases or microtumors and can be demonstrated with a gamma-camera or similar techniques, known to the expert. In this way, not only the position of a tumor or metastases can be determined but also there sizes.

Furthermore, the Tumor-M2-PK-specific antibody can be used objectively to conduct medicaments which can lyse maligne cells, for instance metastases or microtumors, to these microtumors in that the appropriate medicament is coupled to the antibody. As lysing substances there can be used, for example, different cytostatica or toxines.

One variation in application is the use of human monoclonal antibodies.

Because the antibody according to the present invention, does not react with other pyruvatekinase-isoenzymes, this therapy does not lead to a considerable killing of non maligne cells, which is always the result of common chemotherapy.

Furthermore the antibody according to the present invention permits the control of a chemo- and/or radiotherapy.

According to the invention, an antibody is provided which specifically reacts with Tumor-M2-PK and does not bind other pyruvatekinase-isoenzymes. With the help of this antibody it is possible to specifically determine Tumor-M2-PK in blood or other body fluids and swabs qualitatively as well as quantitatively. The antibody according to the invention makes it possible that exact indications with regard to Tumor-M2-PK in these samples can be made and, on the other hand, microtumors (metastases) can be detected, which have formed in the body and can lead to big tumors. It is also possible to specifically kill formed tumors.

Further, it is possible to determine the degree of malignancy and the digity of a tumor or tumor tissue via the amount of Tumor-M2-PK measured, since there is a correlation between the content of Tumor-M2-PK in the tumor cells and the malignancy of these cells.

The following Examples are given for the purpose of illustrating the present invention.

Production of Monoclonal Antibodies

Example 1

Highly purified human Tumor-M2-PK is dissolved in PBS and mixed with an equal amount of Freund's adjuvant. 100 µg amounts of this mixture are injected i.p. and s.c. into 6 to 8 week old Balb/c mice. These injections are repeated twice at intervals of 3 to 4 weeks. Mice immunized according to the above described scheme with highly purified Tumor-M2-PK receive, 3 days before removal of the spleen, an i.v. injection of 100 µg highly purified Tumor-M2PK which is dissolved in PBS.

About 100 million cells from the spleen of an immunized mouse are fused with 50 million myeloma cells (x63-Sp8-653, a cell line which does not synthesise any immune globulin; obtainable from The Salk Institute, Cell Distribution center, San Diego, Calif. 92112, U.S.A.) in the presence of polyethylene glycol (M.W. 3400). fused cells are seeded out on 4 plates, each of which contain 24 cups. Each of these cups contains 50 million spleen cells of nonimmunized syngenic mice in the nutrient medium which contains hypoxanthine, aminopterine and thymidine. The antibody containing supernatants of these fusioned cells (hybridoma) are tested 10 to 14 days later by means of ELISA. westernblot frozen sections, paraffin embedded sections, with regard to their specificity against the following antigen: highly purified human Tumor-M2-PK.

In order to obtain antibodies which are only directed against Tumor-M2-PK, hybridoma cells, the surplus of which does not contain any antibodies directed against other pyruvatekinase isoenzymes, were cloned two times. One of the hybridoma clones isolated in such a way was deposited with ECACC under the designation $M_2PK$ and was given the provisional number ECACC 89 111 606.

Determination of Tumor-M2-PK in plasma with monoclonal, Tumor-M2PK-specific antibodies Example 2

Tumor-M2-PK is determined in plasma with an ELISA. For this purpose, monoclonal, Tumor-M2-PK-specific antibodies from $M_2PK$ obtained according to Example 1, which are dissolved in PBS (pH 7.2), are immobilized on polystyrene as carrier. After a washing step, diluted plasma which contains Tumor-M2-PK is added thereto. The plasma is diluted with a PBS buffer which contains 5 mmole EDTA, 2 µmole EACA, 200 U aprotinine/1 and 0.2% Tween 20 polyethylene. After a washing step in PBS containing 0.1% Tween 20, Tumor-M2-PK bound to the antibody is incubated for 1 hour at ambient temperature with a polyclonal antibody which binds not only Tumor-M2-PK but also other pyruvatekinase-isoenzymes and to which is coupled phosphatase which is dissolved in PBS which contains 0.2% Tween 20 and has a pH of 7.2. After a further washing step, by the addition of p-nitrophenylphosphate disodium salt hexahydrate, a change of the optical density in the reaction vessels is measured in which the monoclonal antibodies have reacted with Tumor-M2-PK.

Determination of Tumor-M2-PK in plasma with two different Tumor-M2-PK-specific-antibodies Example 3

The monoclonal antibody from $M_2PK$ directed against Tumor-M2PK is fixed on to a carrier, as described in Example 2. After a washing step, plasma which contains Tumor-M2-PK is incubated with the monoclonal antibody under the same conditions as in Example 2. After a further washing step, the Tumor-M2-PK is specifically detected by a second Tumor-M2-PK-specific monoclonal antibody from $M_2PK$ II according to the present invention which is directed also against Tumor-M2-PK. This second Tumor-M2-PK-specific antibody carries covalently-bound peroxidase. After a washing step and after the addition of ABTS, as substrate for peroxidase, the change of optical density is measured.

Example 4

The procedure is as described in Example 3, but biotin was coupled on to the second Tumor-M2-PK-specific antibody from $M_2PK$ II instead of an enzyme. Before the addition of substrate, peroxidase-conjugated avidin or peroxidase-conjugated streptavidin was added thereto. The so chosen determination of Tumor-M2-PK permits quite specifically only the determination of Tumor-M2-PK. Other pyruvatekinase-isoenzymes, which are in the solution, do not disturb the determination of the Tumor-M2-PK, according to the present invention.

Example 5

Deposit of the cell culture DSM ACC2155 has been made under the terms of the Budapest Treaty at the DSM Deutsche Sammlung von Mikroorganismen und Zellkulturen GmbH, Mascheroder Weg 1B, D-38124 Braunschweig, Germany on Sep. 23, 1996.

A Tumor-M2-PK-specific antibody from $M_2PK$ obtained according to Example 1, is radioactively labelled. This labelled antibody was added to a solution of 1% BSA in PBS which contained cells of a tumor. The proportion of the antibodies bound to the tumor cells was determined in a scintillation counter. For comparison, to tumor cells-containing buffer radio-actively labelled antibodies which do not react with Tumor-M2-PK were added. A comparison of the results of the scintillimetry showed that the antibodies according to the present invention were specifically bound to the tumor-cells, whereas the control antibodies were not bound to the tumor cells.

We claim:

1. The hybridoma cell line DSM ACC2155.
2. An antibody produced by the cell line of claim 1.
3. A method for the selective determination of a tumor marker, wherein said tumor marker is Tumor-M2-PK, comprising the following steps:
   a) incubating a liquid sample which may contain a tumor marker, Tumor-M2-PK, with at least two different receptors, wherein a first receptor R1 is immobilized to a solid phase and binds Tumor-M2-PK, and a second receptor R2 is in a liquid phase and binds Tumor-M2-PK and carries a label;
   b) separating the solid phase from the liquid phase, and
   c) measuring the label in one of the phases,
wherein, at least one of the receptors is a monoclonal antibody which specifically binds said tumor marker, tumor-M2-PK, and is produced by the hybridoma cell line DSM ACC2155.
4. The method of claim 3 wherein R1 specifically binds tumor-M2-PK, and R2 binds tumor-M2-PK.
5. The method of claim 3 wherein the label is selected from the group consisting of a radioactive compound, an enzyme, a chemiluminescent compound and a fluorescent compound.
6. The method of claim 3 wherein R1 and R2 are monoclonal antibodies.
7. The method of claim 3, wherein both said first and said second receptor are antibodies produced by the hybridoma cell line DSM ACC2155.
8. A method for the selective determination of a tumor marker, wherein said tumor marker is Tumor-M2-PK, comprising the following steps:
   a) providing a sample which may contain Tumor-M2-PK;

b) contacting the sample with 1) a first receptor which binds Tumor M2-PK and is bound to a solid phase and 2) a second receptor which binds Tumor M2-PK and is bound to a label; and c) determining whether binding has occurred;

wherein said first receptor, said second receptor or both said first and said second receptor is a monoclonal antibody which specifically binds the tumor marker Tumor-M2-PK, wherein said antibody is produced by the hybridoma cell line DSM ACC2155.

9. A kit for the selective determination of a tumor marker, wherein said tumor marker is Tumor-M2-PK, comprising:

a) a first receptor R1, which is immobilized to a solid phase and binds Tumor-M2-PK, and a second receptor R2, which is in a liquid phase and binds Tumor-M2-PK and carries a label, wherein at least one of the receptors is a monoclonal antibody which specifically binds said tumor marker, tumor-M2-PK, and is produced by the hybridoma cell line DSM ACC2155.

* * * * *